US005484505A

United States Patent [19]
Isakson et al.

[11] Patent Number: 5,484,505
[45] Date of Patent: Jan. 16, 1996

[54] APPARATUS FOR ATTACHING A FASTENER TO A PROFILED ABSORBENT ARTICLE

[75] Inventors: Cathy L. Isakson; Louis P. Brukhart; Franklin A. Klaene, Jr., all of Cincinnati, Ohio

[73] Assignee: The Procter & Gamble Company, Cincinnati, Ohio

[21] Appl. No.: 439,387

[22] Filed: May 11, 1995

Related U.S. Application Data

[63] Continuation of Ser. No. 320,765, Oct. 19, 1994, abandoned, which is a continuation of Ser. No. 84,047, Jun. 28, 1993, abandoned.

[51] Int. Cl.⁶ .......................... B32B 31/06; B32B 31/12; B32B 31/18; B32B 31/20
[52] U.S. Cl. ........................ 156/470; 156/66; 156/264; 156/289; 156/581; 156/582
[58] Field of Search .............................. 156/583.3, 264, 156/583.5, 66, 553, 470, 581–582, 244.19, 289; 604/389

[56] References Cited

U.S. PATENT DOCUMENTS

| | | | |
|---|---|---|---|
| 2,371,847 | 3/1945 | Saunders et al. | 156/581 X |
| 2,525,980 | 10/1950 | Walters | 156/583.3 X |
| 2,584,002 | 1/1952 | Elser et al. | 156/553 X |
| 2,640,517 | 6/1953 | DeMello | 156/581 X |
| 3,071,180 | 1/1963 | Finger et al. | 156/581 X |
| 3,539,421 | 11/1970 | Crowe | 156/583.3 |
| 3,676,265 | 7/1972 | Edwards | 156/582 X |
| 3,980,016 | 9/1976 | Taylor | 156/583.3 X |
| 4,110,152 | 8/1978 | Dunning et al. | 156/553 |
| 4,761,322 | 8/1988 | Raley | 156/553 X |
| 5,032,206 | 7/1991 | Sigerist | 156/581 X |
| 5,058,497 | 10/1991 | Bishop et al. | 156/582 X |
| 5,133,821 | 7/1992 | Jensen . | |
| 5,234,422 | 8/1993 | Sneller et al. . | |

FOREIGN PATENT DOCUMENTS

| | | |
|---|---|---|
| 0534488A1 | 3/1993 | European Pat. Off. . |
| 1265009 | 3/1972 | United Kingdom ................. 156/583.3 |
| WO93/12747 | 7/1993 | WIPO . |

Primary Examiner—Adrienne C. Johnstone
Attorney, Agent, or Firm—Edward J. Milbrada; Jeffrey V. Bamber; Steven W. Miller

[57] ABSTRACT

A method and apparatus are disclosed for affixing a fastener to the garment side of an absorbent article having a profiled shape, especially an absorbent article that is thicker in the center than at the ends. The method involves placing a fastener with its pressure sensitive adhesive surface adjacent the garment side of the absorbent article, and applying pressure to adhere the pressure sensitive adhesive surface to the garment side of the absorbent article while the absorbent article and the fastener are between a compressible component and an anvil surface. The apparatus comprises a compressible component comprising a surface with a plurality of compressible, resilient elements projecting therefrom in a direction toward an anvil surface.

2 Claims, 3 Drawing Sheets

APPARATUS FOR ATTACHING A FASTENER TO A PROFILED ABSORBENT ARTICLE

This application is a continuation of application Ser. No. 08/320,765, filed on Oct. 7, 1994, now abandoned, which was a continuation of application Ser. No. 08/084,047, filed on Jun. 28, 1993, now abandoned.

FIELD OF THE INVENTION

The present invention is directed to a method of making an absorbent article such as a sanitary napkin, panty liner, or incontinence pad. More particularly, the present invention is directed to a method and apparatus for attaching a fastener, such as a pressure sensitive adhesive fastener, to the garment side of an absorbent article that is "profiled" (e.g., thicker in the center than at the ends).

BACKGROUND OF THE INVENTION

A wide variety of types of structures for disposable absorbent articles used to collect body fluids are known in the art. Commercially available absorbent articles include pad type articles such as sanitary napkins, panty liners, and adult incontinence products. Typically such articles include a liquid pervious topsheet, an absorbent core, a liquid impervious backsheet, and some type of fastener. The fastener often comprises a pressure sensitive adhesive fastener situated on the garment side of the article. The fastener is used for attaching the absorbent article to the crotch region of an undergarment (such as the wearer's panties in the case of a sanitary napkin). The pressure sensitive adhesive fastener is generally covered with a cover strip (or releasable strip) to prevent the adhesive from unintentionally sticking to surfaces other than the wearer's undergarment prior to use.

Absorbent articles having a profiled shape have regions of different caliper that are typically in their absorbent core. Generally, such absorbent articles are thicker in the center than at the ends. These profiled absorbent articles present special problems for attachment of a pressure sensitive adhesive fastener to the garment side of the article during manufacture. The problems become serious when the caliper differences from the leading edge of the core to the center of the core and from center of the core to the trailing edge are so large that it is difficult to supply sufficient pressure over the entire core to adhere the pressure sensitive adhesive fastener properly to the absorbent article.

If the pressure sensitive adhesive is not adhered properly to the garment surface of the absorbent article, when the release paper is peeled off, the adhesive will either be removed from the garment side of the absorbent article with the release paper, or even worse, will stay in the wearer's undergarment when the absorbent article is removed from the undergarment. This problem was previously solved by imparting such high pressures to adhere the fastener to the garment side of the absorbent article so as to risk damaging the absorbent core of the article.

As a result, a need exists for an improved method and apparatus for attaching a fastener to a profiled absorbent article. It is, therefore, an objection of the present invention to provide a method and apparatus for attaching a pressure sensitive fastener to a profiled absorbent article which adequately adheres the fastener to the garment side of the absorbent article without using pressures which are so great that the absorbent article is damaged.

This and other objects of the present invention will be more readily apparent when considered in reference to the following description and when taken in conjunction with the accompanying drawings.

SUMMARY OF THE INVENTION

The present invention relates to a method and apparatus for attaching a fastener to a profiled absorbent article. The method and apparatus essentially involve using a compressible component during the process of applying pressure to attach the fastener to the garment side of the absorbent article. The compressible component compresses or yields more in those places where it is aligned with the portions of the absorbent article having a greater caliper. This equalizes the pressure applied to the pressure sensitive adhesive surface of the fastener to allow for better adherence of the fastener to the garment side of the absorbent article.

The method of the present invention comprises the steps of:

(a) providing an absorbent article having a body-facing side, a garment side, and regions having different calipers;

(b) providing a fastener having two surfaces, at least one of which comprises a pressure sensitive adhesive surface;

(c) providing a compressible component;

(d) providing an anvil surface;

(e) placing the fastener with its pressure sensitive adhesive surface adjacent the garment side of the absorbent article; and (f) applying pressure to adhere the pressure sensitive adhesive surface to the garment side of the absorbent article while the absorbent article and the fastener are between the compressible component and the anvil surface.

The apparatus comprises:

a primary surface which serves as an anvil against which the absorbent article may be placed;

a compressible component comprising a surface with a plurality of compressible, resilient elements projecting therefrom in a direction toward the anvil surface, wherein the primary surface and the elements comprising the compressible component are spaced a distance apart;

a pressure sensitive adhesive fastener applying mechanism; and a mechanism for bringing an absorbent article having a maximum caliper in between the compressible component and the anvil surface while the distance between the elements on the compressible component and the primary surface is less than the maximum caliper of the absorbent article.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings, and in which:

DETAILED DESCRIPTION OF THE INVENTION

1. Description of the Representative Profiled Absorbent Article

Figure 1:
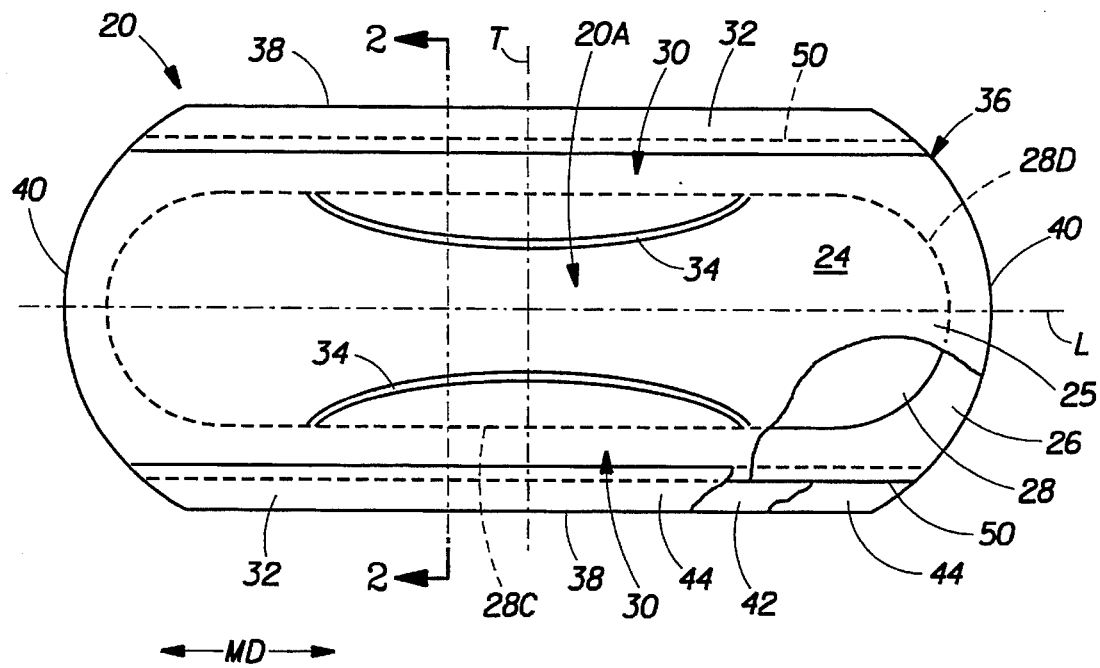
FIG. 1 is a plan view of a representative profiled sanitary napkin that can have a fastener attached by the method of the present invention.

FIG. 1 is a plan view of a preferred type of profiled sanitary napkin 20 that can have its fastener attached by the method and apparatus of the present invention.

The sanitary napkin is shown in its flat-out state with portions of its structure being cut-away to more clearly show the construction of the sanitary napkin 20. The sanitary napkin is shown with the portion of the sanitary napkin 20 which faces the wearer body surface 20A, facing the viewer. As shown in FIG. 1, the sanitary napkin 20 comprises a liquid pervious topsheet 24, a liquid impervious backsheet 26 joined with the topsheet 24, an absorbent core 28 positioned between the topsheet 24 and the backsheet 26, a side flap (or "side margin") 30 extending outwardly from and along the side edges 28C of the absorbent core 28, elastic members 32 joined to the side flaps 30, and embossed channels 34.

FIG. 1 shows a preferred embodiment of the sanitary napkin 20 in which the topsheet 24 and the backsheet 26 have length and width dimensions generally larger than those of the absorbent core 28. The topsheet 24 and the backsheet 26 extend beyond the edges of the absorbent core 28 to thereby form not only the side flaps 30 but also portions of the periphery 36 of the sanitary napkin 20. The periphery 36 defines the outer perimeter or, in other words, the edges of the sanitary napkin 20. The periphery 36 comprises the longitudinal side edges 38 and the end edges 40. (It should be understood that while the absorbent article is shown in the form of a sanitary napkin, the method described herein can also be used to attach a fastener to other types of absorbent articles such as panty liners, incontinence pads, and the like.)

The sanitary napkin 20 has a longitudinal centerline and a transverse centerline, designated L and T, respectively, in FIG. 1. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 that is generally perpendicular to the longitudinal direction.

These terms may also be used interchangably with the terms machine direction and cross-machine direction (abbreviated "MD" and "CD", respectively). The term "machine direction" refers to the direction of product flow through the process of making the sanitary napkin. The sanitary napkin preferably goes through the process with its longitudinal centerline oriented in the machine direction. The term "cross-machine direction" refers to a direction perpendicular to the direction of product flow in the process of making the sanitary napkin.

Figure 2:
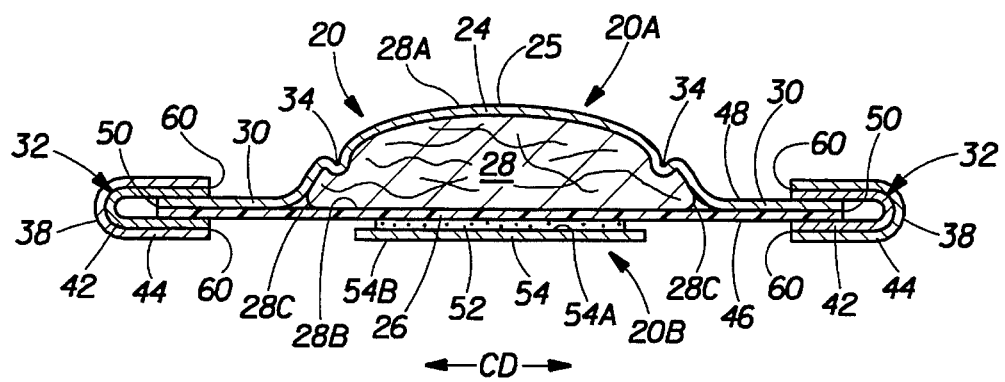
FIG. 2 is a cross-sectional view of the sanitary napkin taken along line 2—2 of FIG. 1.

FIG. 2 is a cross-sectional view of the sanitary napkin 20 taken along section line 2-2 of FIG. 1. FIG. 2 shows the topsheet 24 and the backsheet 26 extending laterally across the entire cross-section to form each side flap 30. The absorbent core 28 is positioned between the topsheet 24 and the backsheet 26 such that the topsheet 24 and the backsheet 26 encase the absorbent core 28. The absorbent core 28 has a body-facing side 28A, a garment-facing side 28B, a pair of longitudinal side edges 28C, and a pair of end edges 28D. The embossed channels 34 are shown in FIG. 2 as being a region of the sanitary napkin 20 wherein preferably both the topsheet 24 and the absorbent core 28 are compressed.

The absorbent core 28 is typically made out of a material that is compressible. The absorbent core 28 is generally shown in FIG. 2 as being thicker in the center than at its edges (i.e., it is profiled in the lateral direction). The absorbent core 28 is also profiled so that it is thicker in the center than at its ends (i.e., it is profiled in the longitudinal direction). The differences in caliper in the longitudinal direction vary in a somewhat more gradual fashion along the length of the sanitary napkin, however, than across the width shown in drawing FIG. 2.

FIG. 2 also shows that the garment surface 20B of the sanitary napkin 20 is provided with a fastener, such as a pressure sensitive adhesive fastener 52 for attaching the sanitary napkin 20 to the wearer's panties. The adhesive fastener 52 is preferably covered with a release paper 54 to keep the adhesive from sticking to surfaces other than the panties prior to use of the sanitary napkin.

FIG. 2 shows that the elastic members 32 comprise an elastomeric laminate comprising an elastomeric layer 42 and a coverstock layer 44. The elastic members 32 each have a pair of longitudinal edges 60. One portion of the elastic member 32 is secured to the outer surface 46 of the side flap 30 (i.e., the backsheet 26) with the other portion secured to the inner surface 48 of the side flap 30 (i.e., the topsheet 24). The elastic members 32 have been folded about the distal edges 50 of the side flaps 30 such that the elastic members 32 form the longitudinal edges 38 of the sanitary napkin 20. The contraction of the elastic members 32 causes the side flaps 30 to stand-up (fold upwardly toward the topsheet 24) to form a wall that acts as a lateral barrier to the flow of menstrual fluids.

The sanitary napkin 20 is, thus, provided with elasticized side flaps by operatively associating an elastic member on both the upper surface and the lower surface of the side flaps. Since the coverstock layer is on the outside of the product, the sanitary napkin is provided with soft side edges which contact the wearer during use. In addition, the elastomeric laminate provides relatively low tension that while being sufficient for raising the side flaps of the product to be a barrier against lateral leakage, also maintains the product in a shape which discourages fluid run-off or leakage at the ends of the pad as well as providing a bunching benefit. The sanitary napkin 20 shown in FIGS. 1 and 2 is described in greater detail in allowed U.S. Pat. No. 5,234,422, which is incorporated by reference herein.

Figure 3:
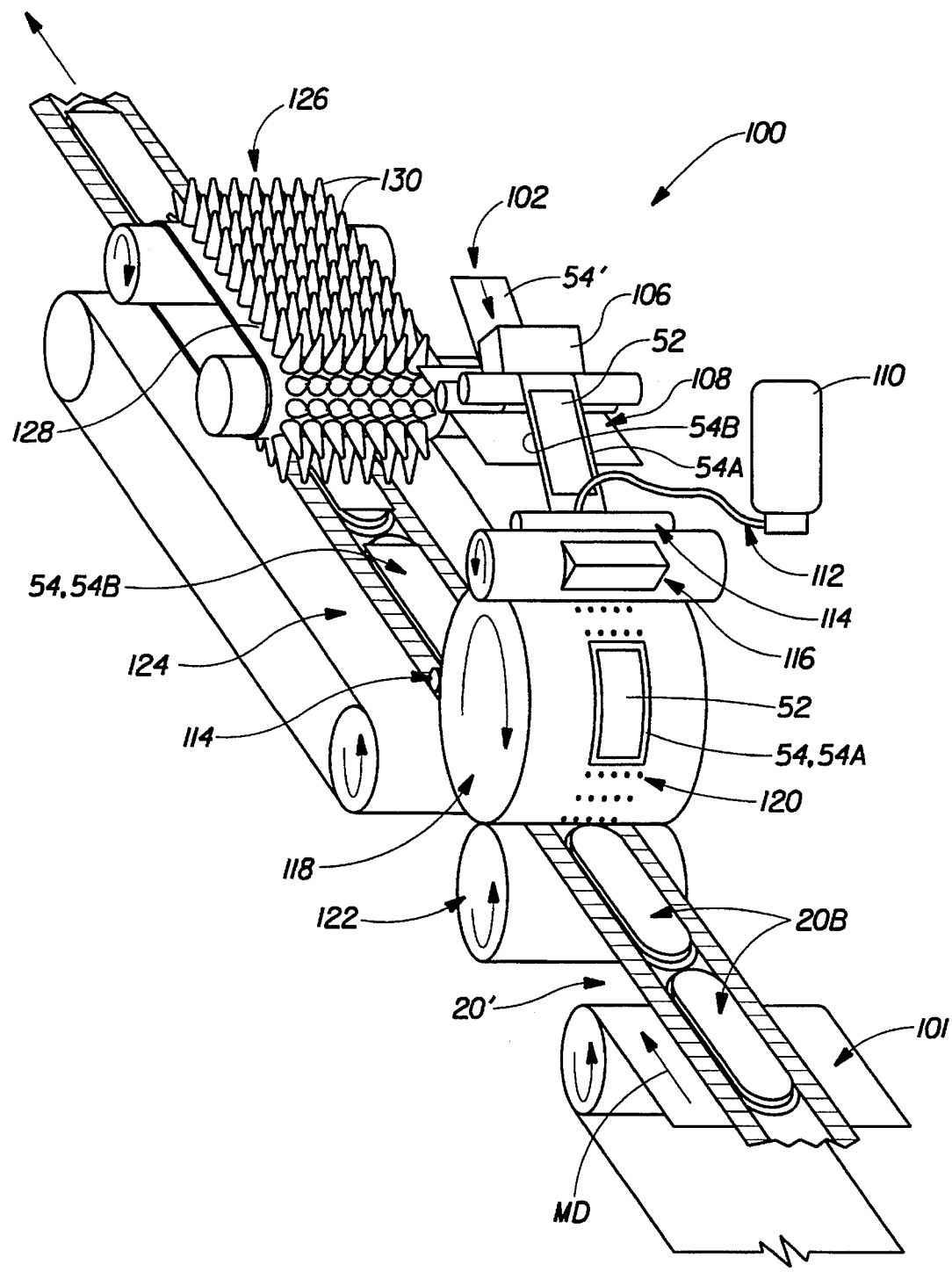
FIG. 3 is a schematic perspective view of a process and apparatus used to attach a fastener to the sanitary napkin shown in FIGS. 1 and 2.

2. Description of the Method and Apparatus for Attaching a Fastener to the Profiled Sanitary Napkin FIG. 3 is a schematic perspective view of a preferred process and apparatus used to attach a fastener to the sanitary napkin shown in FIGS, 1 and 2. The overall apparatus (panty fastener attaching apparatus) is designated by reference number 100.

The panty fastener attaching apparatus 100 preferably generally comprises: a conveyor 101 for bringing in a supply or web 20' of profiled sanitary napkins that are ready to have a fastener added to their garment sides 20B; a source for supplying release paper 102 (or release paper unwind roll, which is out of the picture in FIG. 3); an adhesive applying mechanism 106; a knife 116; a release paper applying mechanism such as a cut and slip vacuum roll 118; a release paper applying anvil roll 122; a fastener applying anvil surface, such as conveyor 124; and a compressible component in the form of an endless belt 126 with a plurality of resilient fingers 130 extending outwardly therefrom.

The sanitary napkins 20 to which the panty fastening adhesive is to be attached come into the process in the form of a continuous web 20' shown in the lower right hand corner of FIG. 3 made by forming means (not shown) with the individual napkins having their garment sides 20B facing upward.

The release paper is brought into the process in the form of a continuous web 54'. The release paper is a 25–30 lb. basis weight sheet of paper that has an inwardly-facing side 54A that will be applied against the panty fastener and an outwardly-facing side 54B that will be exposed to the consumer. The inwardly-facing side 54A of the release paper 54 is silicone-coated to permit the panty fastening adhesive 52 to release therefrom.

The release paper web 54' passes under an adhesive applying mechanism, such as glue gun 106, with the inwardly-facing side of the web facing upward. A glue collection plate 108 is under the glue gun 106. The glue gun 106 has a slot extrusion head (that is not visible in FIG. 3) having a slot with an opening with a height of about 0.007 inch (about 0.18 mm) for applying the panty fastening adhesive to the release paper web 54'.

The panty fastening adhesive comes in from a standard supply source (not shown) and is slot extruded onto the release paper web 54' through the slot in the head of the glue gun 106. The release paper web 54' is in intimate contact with the slot extrusion head during this portion of the process. The extrusion head forces the adhesive out under pressure onto the release paper. The application of the adhesive is intermittent and in the form of the desired pattern (such as a single patch of adhesive, two parallel strips of adhesive, etc.).

The release paper with the panty fastening adhesive 52 coated thereon then travels on to the cut and slip vacuum roll 118. The purpose of the cut and slip vacuum roll is to cut the adhesive coated release paper web 54' into individual release paper sheets and properly space the sheets for application to the individual sanitary napkins in the continuous web 20'. The cut and slip vacuum roll 118 is a roll that is provided with a plurality of vacuum holes 120 through which a vacuum is drawn from a standard vacuum source (the vacuum source is not visible in FIG. 3).

The cut and slip vacuum roll 118 allows the release paper web 54' to slip on its surface before the web is cut (that is, the cut and slip vacuum roll 118 will rotate faster than the release paper web 54') so that the continuous release paper web can be spaced apart for application to the garment sides 20B of the individual sanitary napkins. The release paper web 54' will slip on the cut and slip vacuum roll 118 (that is, the release paper web 54' will not rotate with the vacuum roll 118) until such time as the knife blade 116 passes through and cuts the release paper web 54'. FIG. 3 shows that the knife blade 116 is coated with mineral oil to facilitate cutting and to extend the life of the knife using a system comprising mineral oil supply container 110, mineral oil supply hose 112, and mineral oil application rolls 114.

When a sheet of the web 54' is cut off, the portion of the cut and slip vacuum roll with the vacuum holes will exert a vacuum on the sheet, and the cut sheet of release paper will adhere to the cut and slip vacuum roll and turn at the same speed as the cut and slip vacuum roll 118. The web 20' of sanitary napkins then comes in underneath the vacuum roll 118 and the vacuum on the individual release paper is cut off as it comes in contact with the garment side 20B of the napkin, and the sheet of release paper is transferred to the web of pre-formed sanitary napkins. That allows the distance between release papers to be spaced to the desired fixed distance between the sanitary napkins in the continuous web 20'.

The sanitary napkin with the individual release paper against its garment side 20B then passes through a nip between the cut and slip vacuum roll 118 and an anvil roll 122. Although some pressure is applied in the nip between the vacuum roll 118 and the anvil roll 122, the sheet of release paper 54 is not subjected to sufficient pressure to adhere it to the garment side of the sanitary napkin until it goes through the apparatus described below for attaching the fastener to the absorbent article.

Figure 4:
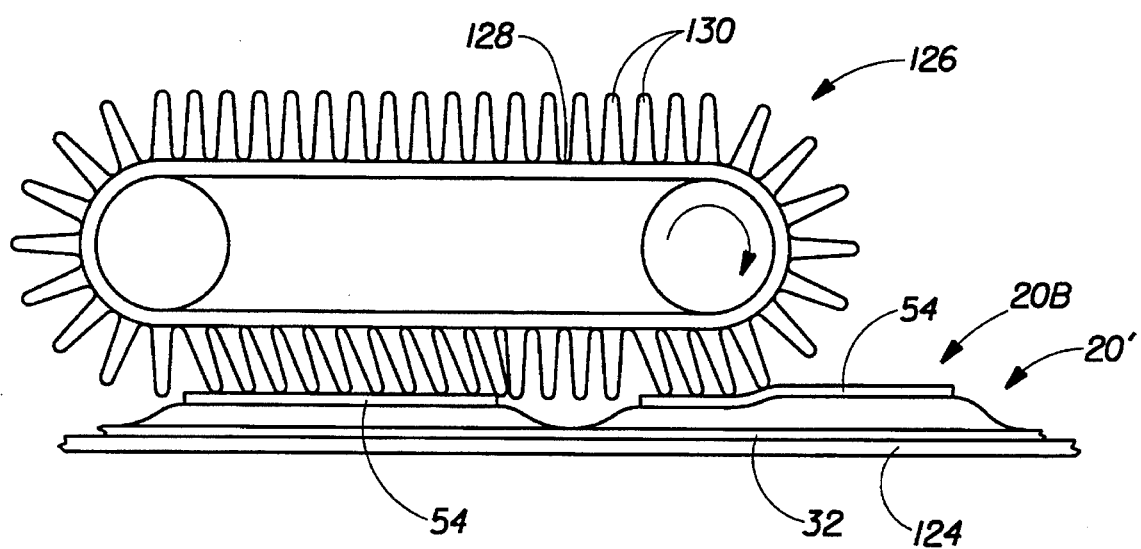
FIG. 4 is a simplified schematic side view of the compressible fastener applying component in FIG. 3.

The apparatus for attaching the fastener to the absorbent article comprises a compressible component 126 and an anvil surface 124. In the preferred embodiment shown in FIGS. 3 and 4 of the drawings, the compressible component 126 is a continuous belt that has pyramid or cylindrical-type fingers 130 that stick out and protrude from the surface 128 of the belt as much as an inch or an inch and a half. There are several thousand of these fingers very tightly spaced over the length of the belt.

The sanitary napkins, as noted above, have a profiled shape with regions of different caliper that are typically in their absorbent core. Generally, such absorbent articles are thicker in the center than at the ends. These profiled sanitary napkins present special problems for attachment of a pressure sensitive adhesive fastener to the garment side of the napkin during manufacture. The problems become serious when the caliper differences between the leading and trailing edges of the core and the center of the core are so large that it is difficult to supply sufficient pressure over the entire core to adhere the panty fastening adhesive properly.

If the pressure sensitive adhesive is not combined properly with the garment surface of the sanitary napkin, when the release paper is peeled off, the adhesive will either be removed from the garment side of the sanitary napkin with the release paper, or even worse stay in the panties when the napkin is removed from the panties. This problem was previously solved by imparting such high pressures to adhere the fastener to the garment side of the sanitary napkin so as to risk damaging the absorbent core of the napkin.

The purpose of the fingers on the belt 126 is to allow this belt to supply pressure on the pad and panty fastening adhesive that is in proportion to the caliper of the core. The fingers will bend where the caliper of the core is higher and will not bend as much where the caliper of the core is lower. The belt 126 supplies an equal force across the entire pad in order to keep the transfer problems described above from occurring.

Numerous alternative embodiments of the process and apparatus of the present invention are possible. In alternative embodiments, the steps of the process can be performed in many other orders and in many other manners, all of which are within the scope of the present invention. For instance, any other means (such as spraying, etc. instead of extruding) can be used to apply the panty fastening adhesive to the release paper web. In other alternative embodiments, the panty fastening adhesive can be applied directly to the garment side 20B of the sanitary napkin, rather than to the inwardly-facing side of the release paper and the inwardly-facing side of the release paper subsequently adhered to the garment side of the sanitary napkin.

In other alternative embodiments, the fastener need not be a strip of pressure sensitive adhesive. The fastener, instead, can be a mechanical fastener with a pressure sensitive adhesive backing. In other alternative embodiments, the method and apparatus of the present invention can be used to attach other components of the absorbent article together in addition to, or alternatively to using the same for applying the fastener to the garment side of the article. For example, the same problems described herein may be presented when attaching the topsheet or the backsheet to a profiled absorbent core. The method and apparatus of the present invention are, thus, suitable for attaching any components together where there is a need to equalize pressure over a given area due to caliper (and/or compressibility) differences of one or more of the components.

The present method and appartus are also not limited to being used with pressure sensitive adhesives. The present method and apparatus are suitable for attaching any components where pressure is required during the attachment process. The method and apparatus of the present invention can also be used to attach components of absorbent articles that are profiled in many other possible manners (such as absorbent articles that are thicker at the ends than in the center).

In addition, the compressible component is not limited to being in the form of an endless belt with pyramid or cylindrical-type fingers. The compressible component can, by way of example, comprise a roll or a flat suface with fingers protruding therefrom. The fingers can be of other suitable shapes. In fact, the compressible component is not limited to a structure with protruding finger-like elements. The compressible component can comprise any type of component that is compressible. Again, by way of example, and not intending to limit the scope of the present invention, the compressible component can comprise a compressible rubber or foam layer, a compressible rubber or foam covered roll or belt, or the like.

While particular embodiments of the present invention have illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus for affixing a strip of pressure sensitive adhesive to a compressible absorbent article that has a maximum caliper and regions of different caliper and compressibility, said apparatus comprising:

means for forming said absorbent article;

a primary surface which serves as an anvil against which said absorbent article may be placed;

a compressible component comprising a surface with a plurality of compressible, resilient elements projecting therefrom in a direction toward said primary surface, wherein said primary surface and the elements comprising said compressible component are spaced a distance apart;

a pressure sensitive adhesive fastener application mechanism; and a mechanism for bringing said absorbent article in between said compressible component and said primary surface while the distance between the elements on said compressible component and said primary surface is less than the maximum caliper of the absorbent article.

2. The apparatus of claim 1 wherein said compressible component comprises a continuous belt.

* * * * *

UNITED STATES PATENT AND TRADEMARK OFFICE
CERTIFICATE OF CORRECTION

PATENT NO. : 5,484,505
DATED : January 16, 1996
INVENTOR(S) : Isakson et al.

It is certified that error appears in the above-identified patent and that said Letters Patent is hereby corrected as shown below:

<u>Title page,</u>
Under the "Related U.S. Application Data" section on the face of the patent, please delete "Oct. 19, 1994" and insert therefor -- Oct. 7, 1994 --.

Signed and Sealed this

Sixth Day of November, 2001

*Attest:*

NICHOLAS P. GODICI
*Attesting Officer*  *Acting Director of the United States Patent and Trademark Office*